(12) United States Patent
Syage et al.

(10) Patent No.: US 8,186,234 B2
(45) Date of Patent: May 29, 2012

(54) HAND-HELD TRACE VAPOR/PARTICLE DETECTION SYSTEM

(75) Inventors: Jack A. Syage, Huntington Beach, CA (US); Paul T. Chaney, La Habra, CA (US); Alan K. Junor, Tustin, CA (US)

(73) Assignee: Morpho Detection, Inc., Newark, CA (US)

( * ) Notice: Subject to any disclaimer, the term of this patent is extended or adjusted under 35 U.S.C. 154(b) by 944 days.

(21) Appl. No.: 12/082,638

(22) Filed: Apr. 10, 2008

(65) Prior Publication Data

US 2009/0223310 A1    Sep. 10, 2009

Related U.S. Application Data

(60) Continuation-in-part of application No. 11/639,579, filed on Dec. 15, 2006, which is a division of application No. 11/202,455, filed on Aug. 11, 2005, now Pat. No. 7,299,710.

(51) Int. Cl.
*G01N 1/22* (2006.01)

(52) U.S. Cl. ............... 73/863.12; 73/863.23; 73/864.34; 73/29.05; 73/31.07

(58) Field of Classification Search ............... 73/863.12, 73/863.23, 28.04, 29.05, 31.02, 31.03, 31.07
See application file for complete search history.

(56) References Cited

U.S. PATENT DOCUMENTS

| | | | |
|---|---|---|---|
| 3,950,739 A * | 4/1976 | Campman | 340/628 |
| 4,092,218 A | 5/1978 | Huschka et al. | |
| 4,293,225 A * | 10/1981 | Wheaton et al. | 356/417 |
| 4,580,440 A * | 4/1986 | Reid et al. | 73/31.07 |
| 4,718,268 A * | 1/1988 | Reid et al. | 73/19.01 |
| 4,897,551 A * | 1/1990 | Gersh et al. | 250/461.1 |
| 4,972,957 A | 11/1990 | Liu et al. | |
| 4,987,767 A * | 1/1991 | Corrigan et al. | 73/23.36 |
| 5,092,218 A | 3/1992 | Fine et al. | |
| 5,098,451 A | 3/1992 | Rounbehler et al. | |
| 5,099,743 A | 3/1992 | Rounbehler et al. | |
| 5,123,274 A * | 6/1992 | Carroll et al. | 73/863.12 |

(Continued)

FOREIGN PATENT DOCUMENTS

WO    2008045023 A2    4/2008

OTHER PUBLICATIONS

PCT International Search Report of the International Searching Authority mailed on Sep. 5, 2008 regarding PCT/US2006/031338 filed on Aug. 11, 2006; 1 page.

*Primary Examiner* — Hezron E Williams
*Assistant Examiner* — Samir M Shah
(74) *Attorney, Agent, or Firm* — Armstrong Teasdale LLP

(57) ABSTRACT

A hand held detector system that has a housing with a passage that can receive a sample, and a concentrator that captures the sample. The hand held system further includes a single detector coupled to the concentrator and a fluid system that provides fluid communication between the housing passage and the concentrator, and between the concentrator and the detector. The system is powered by a battery. The system may include a controller that heats the concentrator with a temperature profile that causes a first trace molecule to desorb at a time different from the desorption of a second trace molecule. The system and components may be powered by a battery.

30 Claims, 8 Drawing Sheets

U.S. PATENT DOCUMENTS

| | | | |
|---|---|---|---|
| 5,214,952 A * | 6/1993 | Leggett et al. | 73/1.03 |
| 5,310,681 A | 5/1994 | Rounbehler et al. | |
| 5,345,809 A * | 9/1994 | Corrigan et al. | 73/23.2 |
| 5,356,594 A * | 10/1994 | Neel et al. | 422/54 |
| 5,395,589 A | 3/1995 | Nacson | |
| 5,400,665 A * | 3/1995 | Zhu et al. | 73/863.12 |
| 5,465,607 A * | 11/1995 | Corrigan et al. | 73/23.36 |
| 5,476,794 A * | 12/1995 | O'Brien et al. | 436/92 |
| 5,551,278 A | 9/1996 | Rounbehler et al. | |
| 5,581,356 A * | 12/1996 | Vezard | 356/418 |
| 5,760,314 A * | 6/1998 | Bromberg et al. | 73/863.21 |
| 5,847,291 A | 12/1998 | Green et al. | |
| 5,855,652 A * | 1/1999 | Talley | 96/44 |
| 5,861,316 A | 1/1999 | Cage et al. | |
| 5,914,454 A * | 6/1999 | Imbaro et al. | 95/64 |
| 5,915,268 A * | 6/1999 | Linker et al. | 73/23.2 |
| 5,974,860 A * | 11/1999 | Kuroda et al. | 73/40 |
| 6,087,183 A | 7/2000 | Zaromb | |
| 6,177,678 B1 * | 1/2001 | Brass et al. | 250/461.1 |
| 6,192,766 B1 | 2/2001 | Gardhagen et al. | |
| 6,334,365 B1 | 1/2002 | Linker et al. | |
| 6,345,545 B1 | 2/2002 | Linker et al. | |
| 6,523,393 B1 | 2/2003 | Linker et al. | |
| 6,708,572 B2 | 3/2004 | Jenkins et al. | |
| 6,887,710 B2 * | 5/2005 | Call et al. | 436/53 |
| 7,122,812 B2 * | 10/2006 | Kalley et al. | 250/504 R |
| 7,279,688 B2 * | 10/2007 | Campman | 250/461.1 |
| 7,579,589 B2 * | 8/2009 | Miller et al. | 250/292 |
| 7,599,135 B2 * | 10/2009 | Feng | 359/803 |
| 7,872,752 B2 * | 1/2011 | LeBoeuf et al. | 356/417 |
| 2004/0119975 A1 * | 6/2004 | Ostler et al. | 356/318 |
| 2005/0160838 A1 | 7/2005 | Weaver | 73/863.03 |
| 2005/0241416 A1 * | 11/2005 | DeFriez et al. | 73/863.12 |
| 2005/0247892 A1 | 11/2005 | Davis | 250/504 H |
| 2006/0218987 A1 * | 10/2006 | Campman | 73/23.2 |
| 2007/0034024 A1 * | 2/2007 | Syage | 73/863.12 |
| 2007/0163327 A1 * | 7/2007 | Mansson | 73/31.02 |

\* cited by examiner

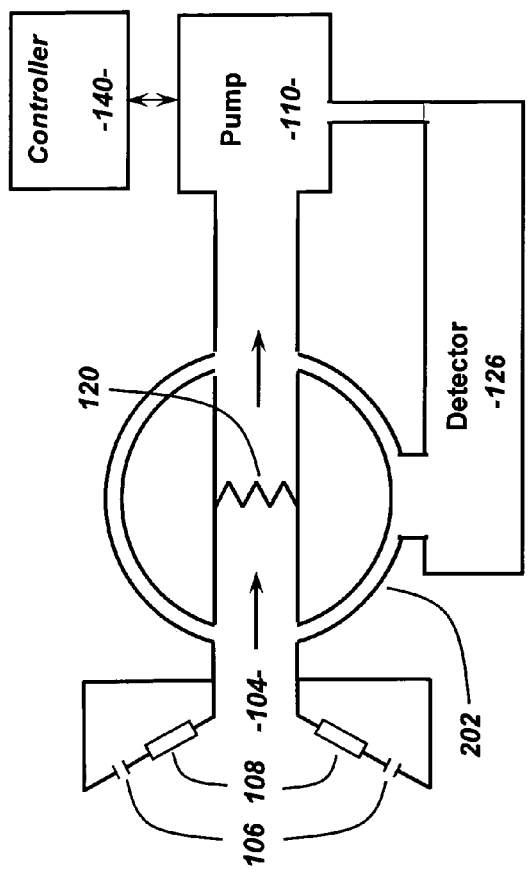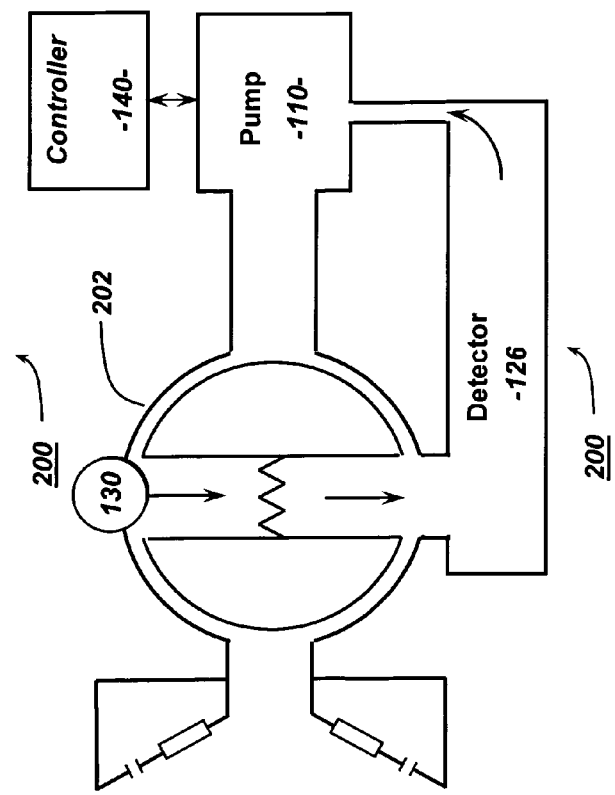

HAND-HELD TRACE VAPOR/PARTICLE DETECTION SYSTEM

CROSS REFERENCE TO RELATED APPLICATIONS

This application is a continuation-in-part of application Ser. No. 11/639,579 filed on Dec. 15, 2006, pending, which is a divisional of application Ser. No. 11/202,455, filed on Aug. 11, 2005, now U.S. Pat. No. 7,299,710.

BACKGROUND OF THE INVENTION

1. Field of the Invention

The present invention relates to the field of detection apparatus used to screen for the presence of explosives and other chemical entities.

2. Background Information

Screening system for threat compounds such as explosives as well as chemical and biological weapons must be able to collect, concentrate, and analyze trace samples quickly and accurately. Many detection technologies such as mass spectrometry (MS), ion mobility spectrometry (IMS), gas chromatography (GC), optical spectroscopy, etc. have been developed over the years and trace detectors now exist that can detect a wide range of explosives and chemical weapons, and to a lesser extent biological weapons. Much less attention has been given to collecting and delivering sample to the detectors, yet collection and delivery is arguably the most challenging part of a screening system since it must adapt to a wide range of applications and screening scenarios. Furthermore, whereas the specificity of a detector is the key to minimizing false positive rates, the collector/concentrator is of vital importance for maximizing detection rates, since if a trace sample is not delivered to the detector, it will result in a non-detect event.

An effective sampling system should preferably have the following operational characteristics: (1) access the volume containing the contamination, (2) dislodge the contamination, particularly for particles that can stick tightly to materials, (3) concentrate collected vapor and particle material, (4) deliver the material to a trace detector in a step that involves vaporization, and (5) minimize cycle time and carryover effects.

An effective collector/concentrator sampling system for explosives and other threats must be able to collect vapor and particles, and if delivering to a trace detector, convert the particles to vapor. Several vapor and particle sampling systems have been developed in the past, however, they are either optimized for one or the other phase, or are not suitable for trace detectors.

U.S. Pat. No. 6,087,183 issued to Zaromb discloses a method to collect vapor and particles on a liquid film. However, a liquid concentrate is not the preferred medium for a trace detector, which is designed to analyze vaporized sample. U.S. Pat. No. 5,914,454 issued to Imbaro et al. discloses a spray of charged droplets to collect vapor, liquid, and particles, but the sample is also concentrated in a liquid. U.S. Pat. No. 5,855,652 issued to Talley discloses a method for collecting particles and microorganisms into a water sample. U.S. Pat. No. 4,092,218 issued to Fine et al. discloses a method for the selective detection of explosives vapors, but does not show that it is capable of collecting particles.

A series of patents issued to Linker et al. disclose methods to collect explosives particles for trace detectors that have some capability to collect vapor as well. U.S. Pat. No. 6,345,545, issued to Linker et al., discloses a two-stage pre-concentrator that uses a metal or other electrically conducting screen to capture particles. Some vapors may also stick to the screen, however, the surface chosen for particle collection is not in general optimal for vapor collection. U.S. Pat. No. 6,523,393, issued to Linker et al., discloses a hand-portable embodiment of the metal screen particle concentrator that makes use of a removable screen that is manually placed first in the high volume flow region and second in the detector region.

The above patents disclose various techniques for sample concentration. Another important component to an overall screening system is a sampling probe for collecting vapor and particles, particularly from hard-to-remove locations and surfaces. U.S. Pat. Nos. 6,334,365 and 5,915,268 issued to Linker et al., disclose the use of air-jets to help dislodge particles from the clothing of individuals in a portal device for screening people for explosives. U.S. Pat. No. 6,708,572, issued to Jenkins et al., also discloses the use of air-jets to dislodge particles from individuals in a portal device.

Trace detectors are used extensively in airports and other venues to screen baggage for explosives. The method typically used to remove material from surfaces are swipes of cloth. This method is effective at collecting residue, however, it requires manual operation and therefore may produce unpredictable results in the collection process. Furthermore it is not effective at collecting vapors.

Another need for threat detection is an efficient means to deliver the collected sample to the detector. U.S. Pat. No. 7,299,710 issued to Syage discloses a system to collect vapor and particle samples onto a removable concentrator that could be inserted into a trace detector. It is desirable to integrate a detector with the sampling system in order to have a combined handheld sampler/detection system. Various systems in the past have been developed based on IMS or GC detection. However, these methods generally only collect vapor or particles and not both. In cases where both vapor and particles are collected, these samples would be delivered to separate detectors and not a single detector. Furthermore, these devices did not provide a means to obtain a second dimension of separation in order to improve analysis accuracy.

BRIEF SUMMARY OF THE INVENTION

A hand held detector system that has a housing with a passage that can receive a sample, and a concentrator that captures the sample. The hand held system further includes a single detector coupled to the concentrator and a fluid system that provides fluid communication between the housing passage and the concentrator, and between the concentrator and the detector.

BRIEF DESCRIPTION OF THE DRAWINGS

FIG. 2A-B are illustrations of another embodiment of a vapor/particle sampling and detection system;

DETAILED DESCRIPTION OF THE PREFERRED EMBODIMENT

Disclosed is a hand held detector system that has a housing with a passage that can receive a sample, and a concentrator that captures the sample. The hand held system further includes a single detector coupled to the concentrator and a fluid system that provides fluid communication between the housing passage and the concentrator, and between the concentrator and single detector. The system may be powered by a battery. The system may include a controller that heats the concentrator with a temperature profile that causes a first trace molecule to desorb at a time different from the desorption of a second trace molecule. The temperature profile allows the trace molecules to be sent separately to the detector, which improves the accuracy of trace detection. The system components may be powered by a battery.

The system contains filter components for collecting and concentrating vapor and particles from objects and surfaces and a detector to analyze the collected sample. The system housing may emit air-jets to help dislodge particles from surfaces and a heating lamp to help vaporize compounds on surfaces or objects. The sampling system is especially useful for screening explosives and other illicit chemicals and toxins on people, baggage, cargo, and other objects.

The disclosed system is unique in being able to collect particles and vapors off of surfaces, concentrate the sample onto a concentrator and deliver the sample to a single detector for analysis all in one hand held unit. The handheld unit further has temperature programmed desorption for improved analysis accuracy, and a reusable sample cartridge that can be adapted to other external detection systems.

Figure 1A:
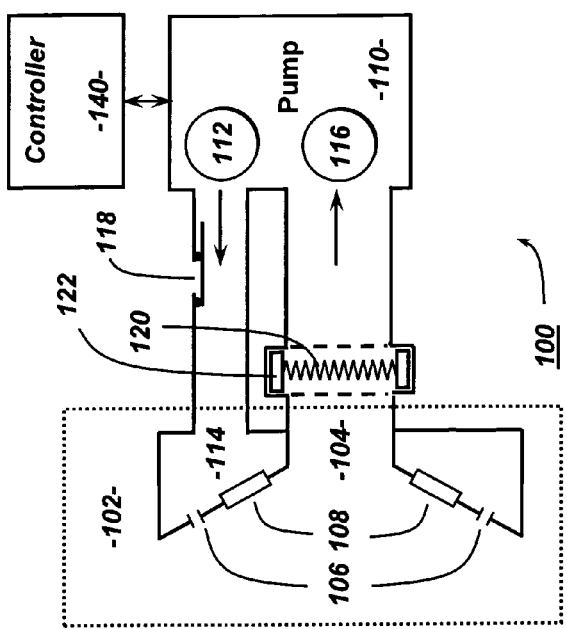
FIGS. 1A-C are illustrations of a vapor/particle sampling and detection system.
Figure 1B:
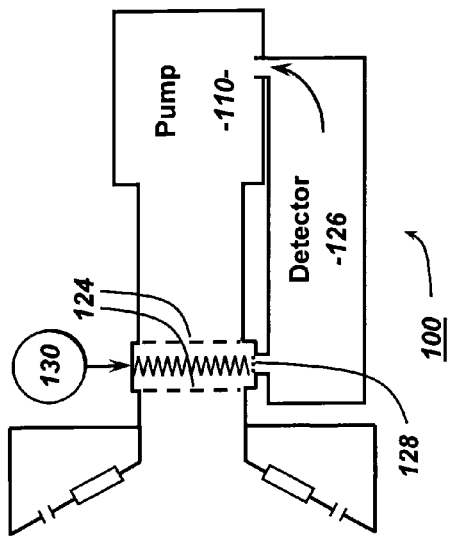
Figure 1C:
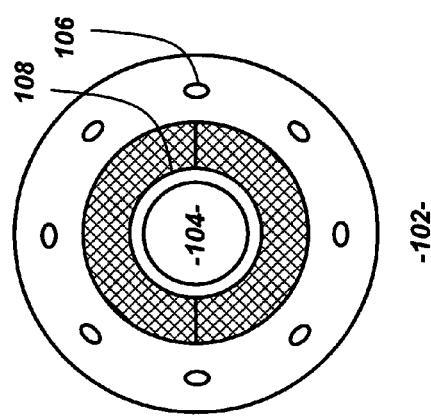

Referring to the drawings more particularly by reference numbers, FIGS. 1A-C show an embodiment of a collection and detection system 100. The system 100 includes a sampling head 102 that has an intake port 104 and a plurality of air-jet nozzles 106. The head 102 may also have a heater assembly 108. The assembly 108 may have one or more heat lamps. The position of the air-jet nozzles 106 and the lamps 108 can be reversed from what is shown, or can have other configurations. The system 100 may include a pump 110 that creates a positive pressure air flow 112 in passage 114 to pressurize the air-jet nozzles 106 and a negative pressure air flow 116 to pull sample through the intake port 104. For the embodiment shown in FIGS. 1A-C, the pumping action may be continuous during sample collection such that air-jets are flowing out of the nozzles 106 while sample is being pulled in through the intake port 104. The heater 108 is typically on during the sampling period, however, it may be desirable to turn the heater 108 on for only a part of the sampling period, such as to limit vapor collection to the latter part of the sampling period.

The system 100 may include an exhaust valve 118 that can be opened to drop the pressure within passage 114 and terminate the flow of the air-jets from nozzles 106, while sample is still being pulled in through the intake port 104. The system 100 includes a concentrator mesh 120 that collects particles and vapor from the sample. Opening the exhaust valve 118 may be useful for cooling the concentrator mesh 120 after an analysis cycle is complete and/or for collecting only vapor from a surface when the heater 108 and pumps 110 are on.

The air-jets are aimed at a surface or object and the air impact loosens particles that are then pulled through the sampling port 104. The heater 108 increases the temperature of the surface or object and provides a corresponding increase in the vapor pressure of more volatile compounds in order to enhance the collection of vapor. The particle and vapor sample is pulled through the concentrator mesh 120. The concentrator mesh 120 collects both particles and vapors. The concentrator mesh 120 can be installed in a removable cartridge 122.

The concentrator 120 may have shutters or valves 124 that can open during sample collection and close during sample delivery to a detector 126 as shown in FIG. 1B. The concentrator 120 can also have a valve or shutter 128 that is closed during sample collection and opened during sample delivery to the detector 126. The sample that is collected on the concentrator mesh 120 is delivered to the detector 126 by thermal desorption, but passing a current through the mesh if it consists of metal, or by other means. The delivery of sample to the detector 126 can be assisted by a pick up flow 130 provided by the overpressure side of the pump 110 or from another source such as a supplemental gas supply. The detector 126 may also use a pump flow from pump 110 to draw the sample into and out of the detector 126. A controller 140 controls all the functions of the sampling and detection system.

FIGS. 2A-B show another embodiment of the system 200 that has a rotary mechanism 202 to switch between sampling flow (FIG. 2A) and detection flow (FIG. 2B). As described in the embodiment shown in FIGS. 1A-C, the detection flow can be assisted by a supplemental flow 130 provided by the pump 110 or another source of positive pressure. The detector flow can also be assisted by the pump 110. The system 200 may also have the exhaust valve 118 described and shown in FIG. 1.

Figure 3:
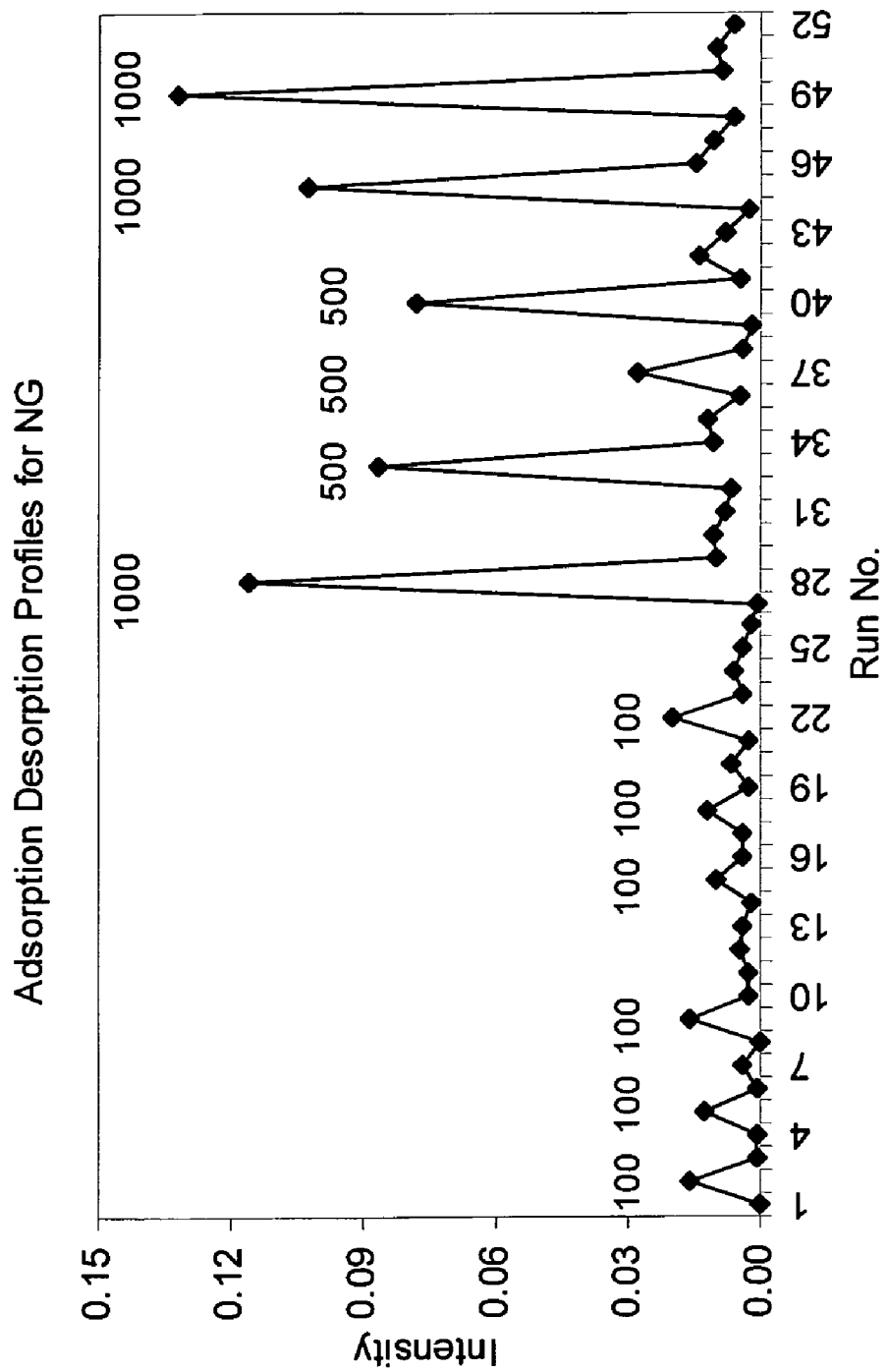
FIG. 3 is a graph showing absorption intensity as a function of runs.

FIG. 3 is a graph that shows the effectiveness of the disclosed particle/vapor concentrator system. The plot shows the detection signal resulting from the collection of nitroglycerin (NG) vapor onto the sample mesh and then thermal desorption into a MS detector. The numbers over the peaks refer to the mass in nanograms of NG that was vaporized into the sampling flow. Based on a detection limit of 2 ng, the results show an efficiency for collection, desorption and introduction into the detector of about 10-30%.

Figure 4:
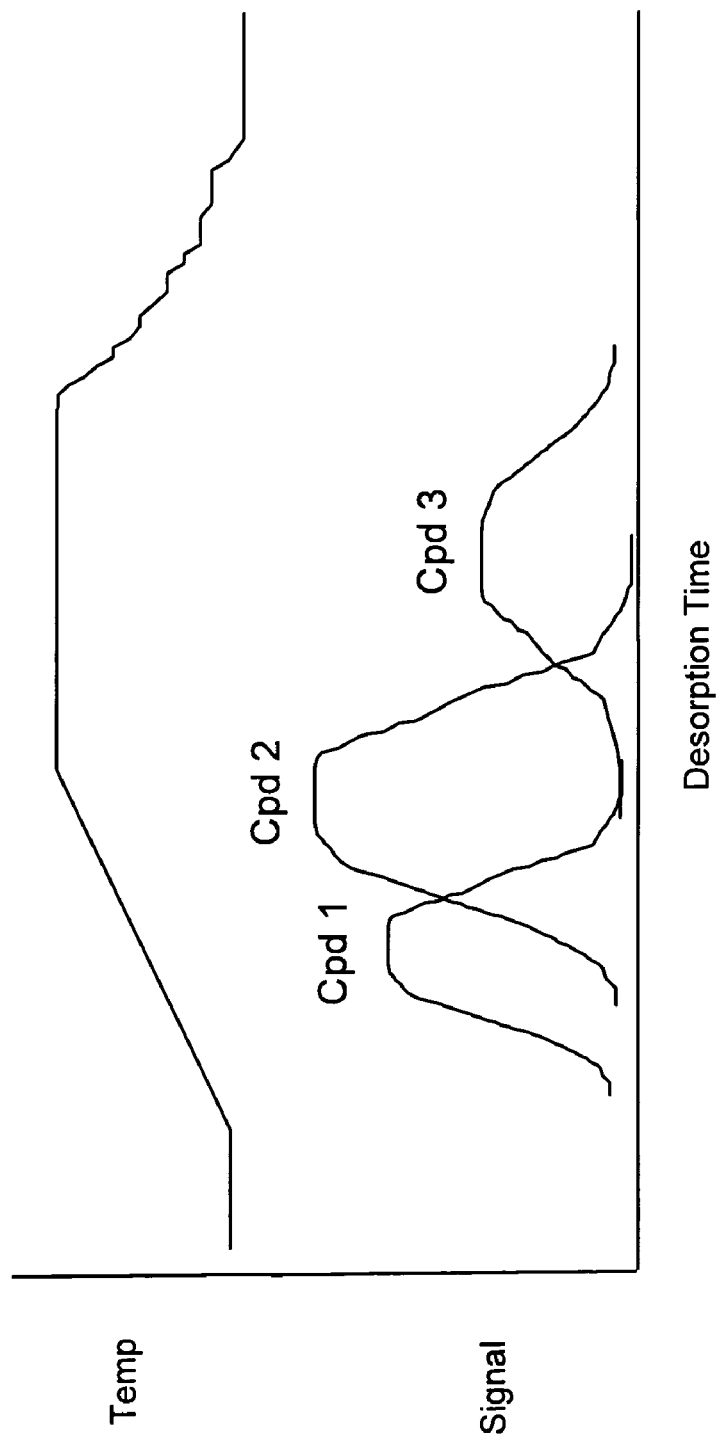
FIG. 4 is a diagram showing a method for temperature programmed thermal desorption of multiple collected compounds.

There are many types of trace detectors for analyzing compounds that have been desorbed into the vapor phase. MS is the most accurate detector, however, such detectors cannot be reduced in size and weight enough to be used for a handheld detection system. Historically hand held detectors have utilized, IMS, GC, or some other simple detector. These devices have low resolution and if presented with a very complex mixture can give many overlapping signals. This can lead to false positive responses when an interferent overlaps with the expected signal for a targeted threat compound. The sampling and concentration technology disclosed here collects both particles and vapors and can sample a wide variety of compounds. This can lead to signal confusion with low resolution detectors. This problem is minimize by separating the introduction of the collected sample into the detector using a technique to thermally control the desorption of the sample. By using a programmed temperature ramp on the sample mesh 120, compounds with higher vapor pressure (i.e., lower boiling points) will desorb before compounds with lower vapor pressure. This method is illustrated in FIG. 4, which shows the heating applied to the sample mesh 120 such that the temperature ramps up at a controlled rate. As an example, we show the possible desorption signal of three trace molecules with different vapor pressures. This example shows that it is possible to separate the desorbed sample so that the detector 126 does not have to analyze all the trace molecules at the same time. This method provides a technique to expand the signal from one dimension to two dimensions, which greatly increases the accuracy of a detection system.

Figure 5:
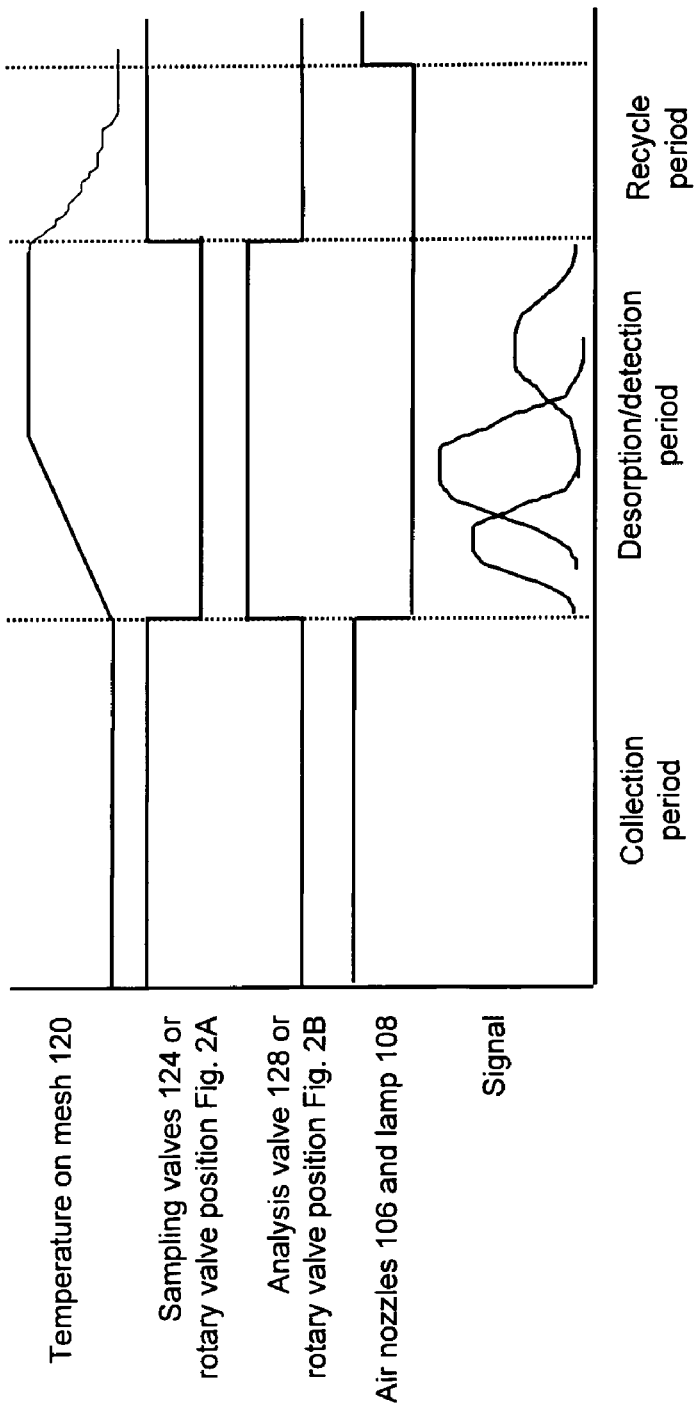
FIG. 5 shows a timing diagram for the sampling and detection system.

FIG. 5 is a timing diagram that shows an entire sequence of sample collection, desorption/detection, and recycle for the handheld detection system. During the collection period, the sampling valve 124 is open, or for system 200 the rotary valve 202 is in the position that allows for sampling flow (FIG. 2A). During the collection period, the air-jets 106 and heating source 108 are on. During the desorption/detection step the sampling valve 124 is closed, or the rotary valve 202 is in position for detection flow (FIG. 2B). The air-jets 106 and heating source 108 are off during this step. The sample mesh 120 is then heated to thermally desorb the collected particles and vapor. FIG. 5 shows a ramped heating rate, as described earlier and illustrated in FIG. 4, in order to separate in time the desorption of the variety of compounds that are collected. Before the next sampling cycle, it may be desirable to clear down the sampling mesh 120 by allowing all compounds to thermally desorb and then cool the mesh 120 with a flow of sample air by actuating the sample valves 124 or 202 in the sample flow position. Another way to cool the sample mesh 120 is to use a thermoelectric device such as a Peltier cooler. The advantage of an active cooler is rapid cooling and also the capability to take the temperature below ambient temperature thereby improving collection efficiency. The timing for the thermoelectric cooling could be the same as that for the activation of the intake port 104.

Figure 6:
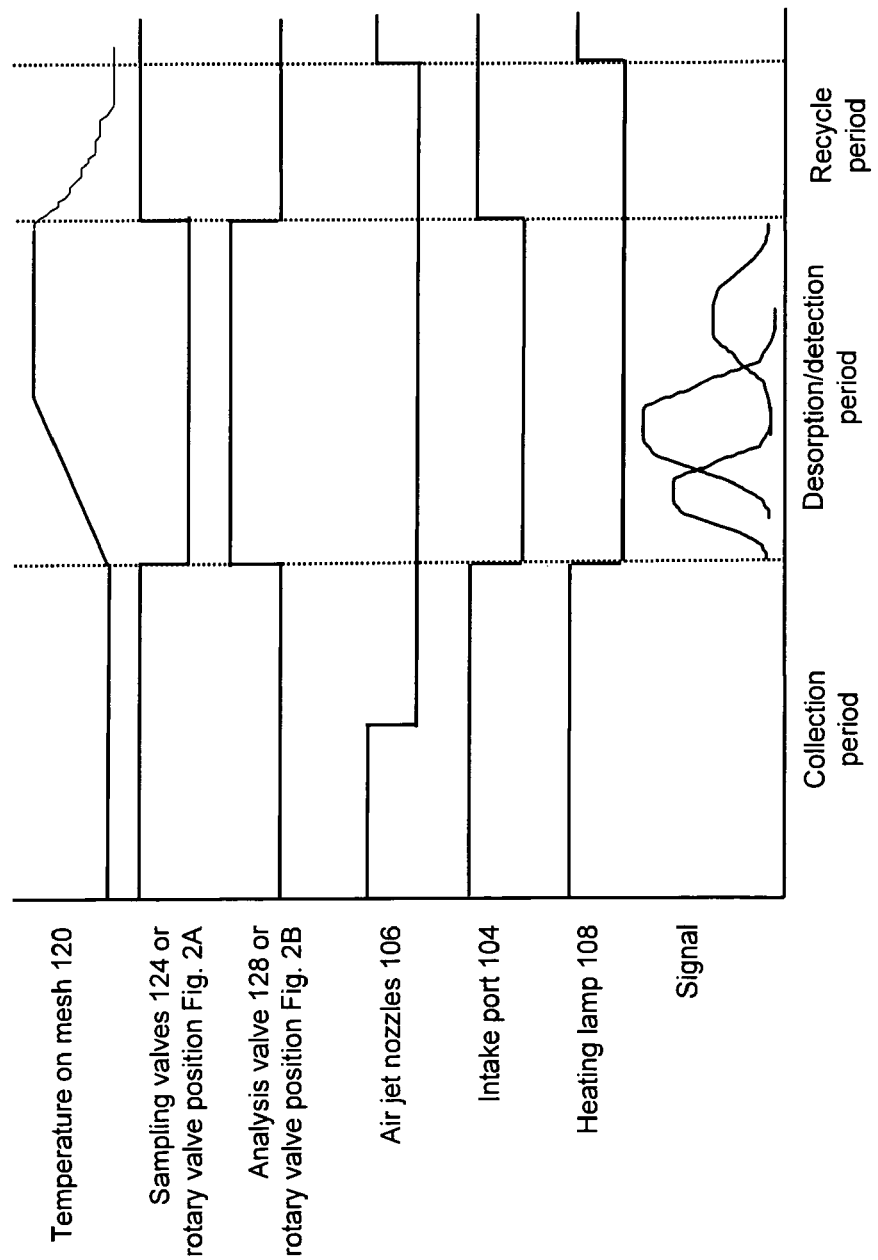
FIG. 6 shows another timing diagram for the sampling and detection system.

FIG. 6 shows a timing diagram for another mode of operation. In this case, the detection system 100 or 200 can be operated such that the collection mesh 120 is cooled after the desorption/detection period by activating the intake port 104 and deactivating the air jet nozzles 106 and heater lamp 108 (e.g. opening the exhaust valve 118). For the next collection period the air jet nozzles 106 can be turned on to collect particles and then turned off after a certain time. For the remainder of the collection period the heating lamp 108 and intake port 104 can remain on for efficient collection of vapor. The idea is that the air jet nozzles have finished collecting particles over the sampling area, but the vapor pressure of compounds over the sampling area are just reaching significant levels and these are best collected without the air jet stream, which can dilute the vapor. Another method is to turn the air jet nozzles 106 on for a series of short intervals or bursts. In this way, particles can be loosened from surfaces, but without the concern that a continuous air jet might sweep particle and vapor sample material away from the intake port 104.

U.S. Pat. No. 7,299,710 issued to Syage ("the '710 patent") describes a particle/vapor concentrator that include two parallel meshes. One mesh is constructed from a metal material to collect particles. The other mesh is constructed from a non-metallic chemically adsorbing material for collecting vapor. The metal mesh is heated with a current to vaporize the particles and also to heat the vapor mesh to liberate the vapor.

Figure 7B:
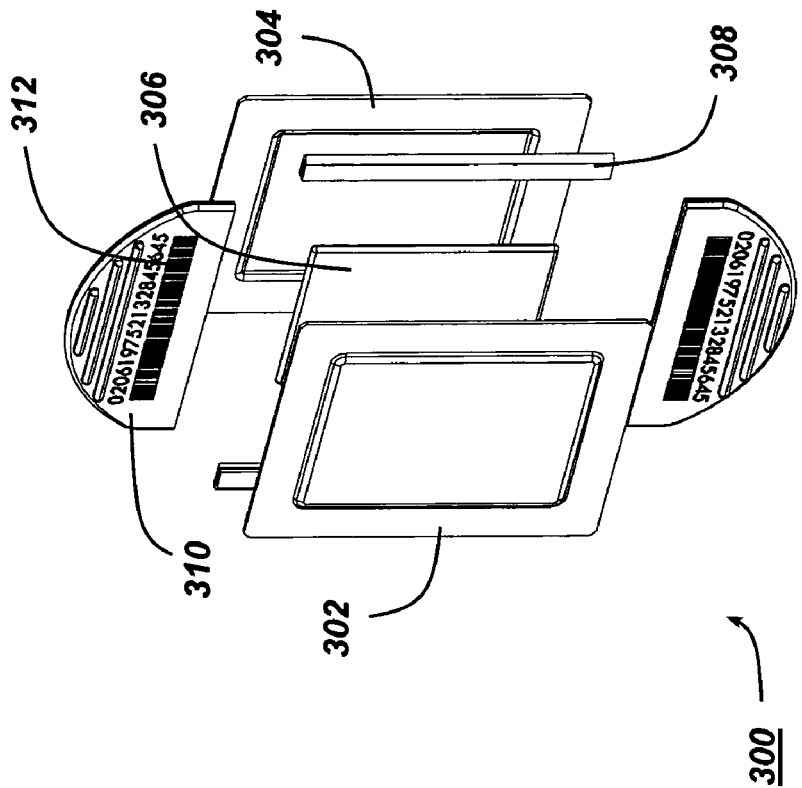
FIGS. 7A-B show an embodiment of a vapor/particle sample cartridge.
Figure 7A:
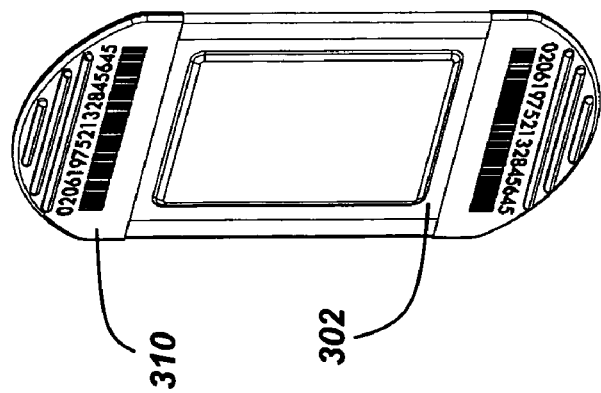

FIGS. 7A-B show an embodiment of a concentrator 300 that includes two metal meshes 302 and 304 that sandwich a chemically adsorbing vapor mesh 306. The mesh sandwich can be held together by a pair of metal bands 308 that can also serve as electrical connectors to receive a current that flows through the metal meshes 302 and 304. The concentrator 300 can have a handling tab 310 for handling and for inclusion of identification markings such as a bar code 312. Alternatively, the vapor mesh 306 can be integral with one or both metal meshes 302 and 304. For example, the vapor mesh 306 may be intertwined into a metal mesh.

The '710 patent describes power requirements for a handheld particle/vapor sampler/concentrator. The systems 100 and 200 add a detection function while still minimizing power so that the systems are hand held devices. The additional requirements for the addition of a detector 126 such as illustrated in FIGS. 1 and 2 are power and sample air flow. IMS, GC, optical, and other compact detectors for vapor analysis have been described. Also described is a variation of IMS, which is often referred to as high-field asymmetric waveform IMS (FAIMS) or differential mobility spectrometry (DMS). The DMS is the most advanced of the detectors listed and we will use this example to establish the power requirements for a handheld detection system. For a handheld sampling system we have demonstrated the use of a 150 L/min pump 110 and operation of air jets 106 and heater 108 that consumes on average 30 W of power. A DMS detector consumes about 10 W average power for a total of 40 W average power during operation. Assuming the use of a standard off-the-shelf rechargeable nickel-cadmium battery than we can obtain 40 Watt-hour of use in about 2 lb. For a 12 s overall cycle time, this would give up to 300 sample analyses per battery charge, which represents a very useful performance. More advanced battery technologies, such as lithium ion can up to double the battery life described above. The system controller can count a number of samples collected and analyzed by the system.

Figure 8:
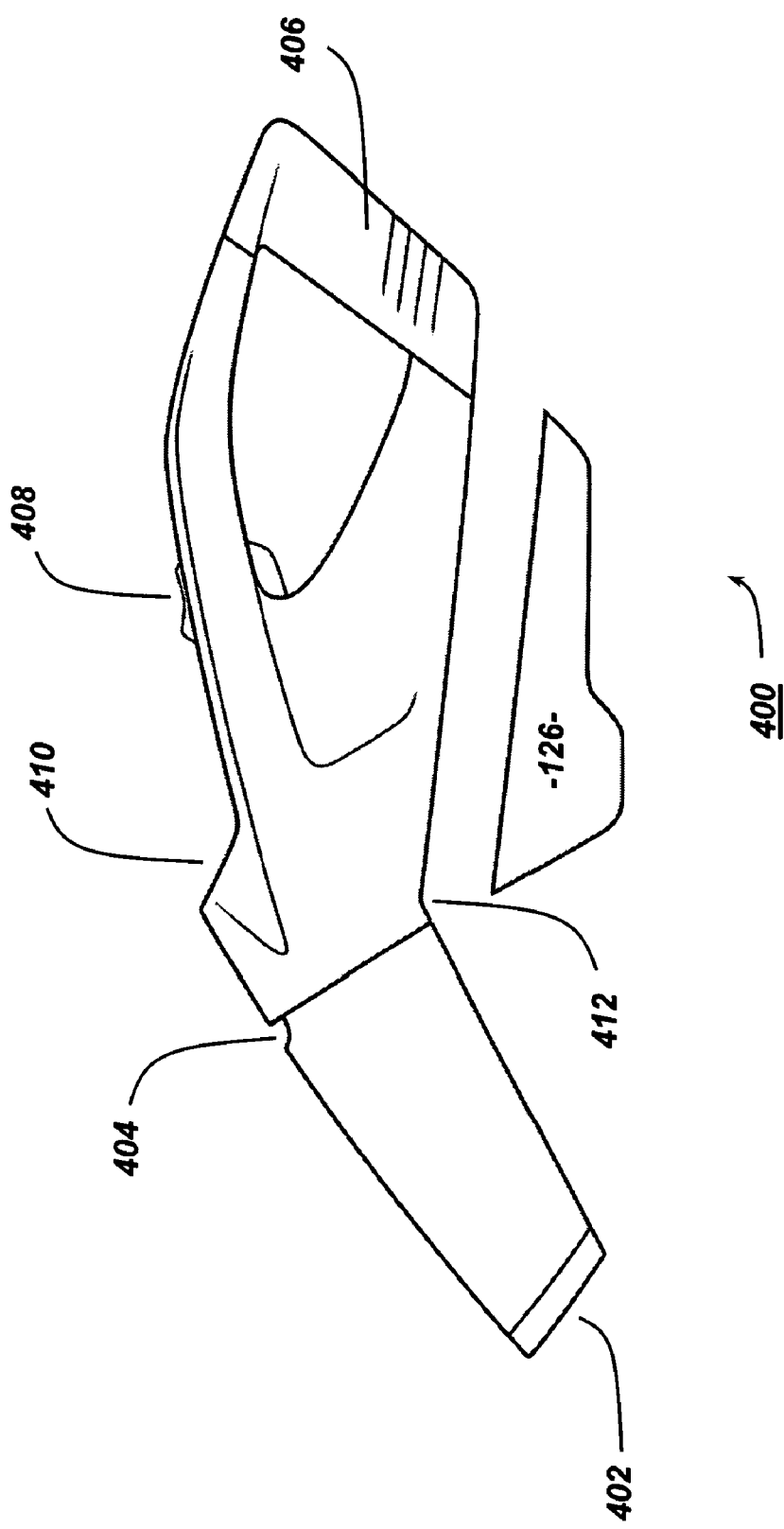
FIG. 8 shows an embodiment of a handheld vapor/particle sampling and detection system.

FIG. 8 shows an embodiment of a handheld trace detection system 400 based on the operation described above and represented in FIGS. 1-7. The intake port is denoted by 402 and contains the air jet nozzles and heater shown in FIGS. 1 and 2. A sample cartridge (not shown) can be loaded through a cartridge slot 404. Power can be provided by a battery 406 and controlled through switch 408. The system 400 can be controlled by a programmable controller and an interface such as a liquid crystal display monitor and touch screen or keypad denoted by 410. The number of collected samples can be displayed by the monitor 410. The detector 126 can mount in various locations, but for this embodiment is shown to mount on the bottom 412 of the handheld unit. Other configurations are possible and this technology can also be configured for non handheld uses such as a desktop analyzer or part of a larger screening system.

The systems and devices shown and described can be utilized to detect samples of trace explosives on baggage, cargo, and personnel due to concealed explosive devices. Trace contamination is known to be pervasive throughout the bomb making and bomb packing process. This contamination can take the form of vapor for more volatile explosives (e.g., the class of nitrate esters and nitro toluenes, as well as taggant compounds) or particles for the more crystalline forms (e.g., the nitramines RDX and HMX).

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed:
1. A hand held detector system, comprising:
a housing with a passage that can receive a sample from at least one of a surface and an object;
a concentrator that captures said sample;
a single detector coupled to said concentrator; and,
a fluid system comprising a pump configured to:
provide a negative pressure fluid flow between said housing passage and said concentrator and between said concentrator and said single detector; and, provided a continuous positive pressure fluid flow directed toward at least one of the surface and the object.

2. The system of claim 1, further comprising a controller that heats said concentrator to a temperature to desorb at least one compound.

3. The system of claim 2, wherein said controller creates a temperature profile that causes a first trace molecule to desorb at a different time than a desorption of a second trace molecule.

4. The system of claim 1, wherein said housing has at least one air-jet nozzle.

5. The system of claim 4, further comprising a heating element located adjacent to said passage.

6. The system of claim 4, wherein said housing has an exhaust valve that is opened during an intake of said sample.

7. The system of claim 1, further comprising at least one valve that sequentially controls fluid communication between said passage and said concentrator, and said concentrator and said single detector.

8. The system of claim 1, wherein said concentrator includes a non-metal mesh located between a pair of metal meshes.

9. The system of claim 1, further comprising a controller that counts a number of samples collected by said concentrator.

10. The system of claim 1, wherein said concentrator is removable and includes a bar code.

11. The system of claim 1, further comprising a battery coupled to said concentrator, said fluid system and said single detector.

12. The system of claim 1, wherein said concentrator includes a non-metal mesh integral with a metal mesh.

13. A detector system, comprising:
a housing with a passage that can receive a sample;
a concentrator that captures said sample;
a controller that heats said concentrator, said controller creates a temperature profile that causes a first trace molecule to desorb at a different time than a desorption of a second trace molecule;
a detector coupled to said concentrator; and,
a fluid system that provides fluid communication between said housing passage and said concentrator and between said concentrator and said single detector.

14. The system of claim 13, wherein said housing has at least one air-jet nozzle.

15. The system of claim 14, further comprising a heating element located adjacent to said passage.

16. The system of claim 14, wherein said housing has an exhaust valve that is opened during an intake of said sample.

17. The system of claim 13, further comprising at least one valve that sequentially controls fluid communication between said passage and said concentrator, and said concentrator and said single detector.

18. The system of claim 13, wherein said concentrator includes a non-metal mesh located between a pair of metal meshes.

19. The system of claim 13, wherein said controller counts a number of samples collected by said concentrator.

20. The system of claim 13, wherein said concentrator is removable and includes a bar code.

21. The system of claim 13, wherein said fluid system includes a single pump.

22. The system of claim 13, wherein said concentrator includes a non-metal mesh integral with a metal mesh.

23. A method for detecting a trace molecule in a sample, comprising:
holding a hand held detector that includes:
a housing with a passage that can receive the sample from at least one of a surface and an object;
a concentrator;
a single detector coupled to the concentrator;
a fluid system that includes a single pump; and,
a battery coupled to the fluid system, the concentrator and the single detector;
inducing a continuous positive pressure fluid flow toward at least one of the surface and the object with the single pump;
pulling a sample through the passage and onto the concentrator using a negative pressure fluid flow induced by the single pump;
desorbing at least one trace molecule from the concentrator; and,
moving the trace molecule to the single detector.

24. The method of claim 23, wherein inducing a continuous positive pressure fluid flow toward at least one of the surface and the object comprises directing at least one air jet to create the sample.

25. The method of claim 24, further comprising applying heat to at least one of the surface and the object.

26. The method of claim 23, further comprising counting the number of samples collected by the concentrator.

27. A method for detecting a trace molecule in a sample, comprising:
pulling a sample through a housing passage and onto a concentrator;
heating the concentrator with a temperature profile that causes a first trace molecule to desorb at a time different than a desorption of a second trace molecule; and,
moving the first and second trace molecules to a detector.

28. The method of claim 27, further comprising directing at least one air jet at an object to create the sample.

29. The method of claim 28, further comprising applying heat to the object.

30. The method of claim 27, further comprising counting the number of samples collected by the concentrator.

* * * * *